(12) United States Patent
Freeman et al.

(10) Patent No.: US 6,741,884 B1
(45) Date of Patent: May 25, 2004

(54) INFRARED ENDOSCOPIC BALLOON PROBES

(75) Inventors: Jenny E. Freeman, Chestnut Hill, MA (US); Charles R. Lambert, Melbourne, FL (US); Michael J. Hopmeier, Mary Esther, FL (US)

(73) Assignee: HyperMed, Inc., Weston, MA (US)

( * ) Notice: Subject to any disclaimer, the term of this patent is extended or adjusted under 35 U.S.C. 154(b) by 0 days.

(21) Appl. No.: 09/389,342

(22) Filed: Sep. 2, 1999

Related U.S. Application Data
(60) Provisional application No. 60/098,957, filed on Sep. 3, 1998.

(51) Int. Cl.[7] ............................................. A61B 5/00
(52) U.S. Cl. .................. 600/473; 600/116; 600/178; 600/182
(58) Field of Search ............................. 600/473, 476, 600/310, 478, 109, 116, 160, 178, 182; 606/15, 16

(56) References Cited

U.S. PATENT DOCUMENTS

| | | | | |
|---|---|---|---|---|
| 4,445,892 A | | 5/1984 | Hussein et al. ............. 604/101 |
| 4,515,165 A | | 5/1985 | Carroll ...................... 128/664 |
| 4,875,897 A | | 10/1989 | Lee .......................... 604/283 |
| 5,879,306 A | * | 3/1999 | Fontenot et al. ............ 600/473 |
| 5,935,075 A | * | 8/1999 | Casscells et al. ........... 600/474 |
| 6,096,030 A | * | 8/2000 | Ortiz ......................... 606/14 |
| 6,200,307 B1 | * | 3/2001 | Kasinkas et al. .............. 606/7 |
| 6,238,339 B1 | * | 5/2001 | Fiddian-Greene et al. .. 600/309 |

FOREIGN PATENT DOCUMENTS

| | | | |
|---|---|---|---|
| EP | 0063431 | 10/1982 | ........... G01N/21/31 |
| EP | 0590268 | 4/1994 | ............ A61B/5/00 |
| EP | 0783867 | 7/1997 | ........... A61B/5/103 |
| GB | 2300045 | 10/1996 | ............ A61B/5/00 |
| WO | WO9215008 | 9/1992 | ........... G01N/21/65 |
| WO | WO9607889 | 3/1996 | ........... G01N/21/64 |
| WO | 9620638 | 7/1996 | ............ A61B/5/00 |

OTHER PUBLICATIONS

Prahl, S. A. et al, "Determination of optical properties of turbid media using pulsed photothermal radiometry", Phys. Med. Biol., 1992, vol. 37, No. 6, 1203–1217, Bristol, UK.

International Search Report for PCT/US98/22961 dated Jul. 6, 1999.

* cited by examiner

*Primary Examiner*—Ruth S. Smith
(74) *Attorney, Agent, or Firm*—Morrison & Foerster LLP (57) ABSTRACT

Balloon probes, adapted for use in endoscopy and other medical procedures, are useful to obtain spectroscopic information reflected or emitted from a tissue of interest in the infrared spectral region. The information collected by the probe is useful in the diagnosis and treatment of disease. The invention also relates to methods utilizing these probes to analyze a surface of interest, in a minimally invasive manner, in connection with the diagnosis and treatment of disease.

52 Claims, 1 Drawing Sheet

INFRARED ENDOSCOPIC BALLOON PROBES

REFERENCE TO RELATED APPLICATIONS

This application claims the benefit of U.S. Provisional Patent Application Serial No. 60/098,957 filed Sep. 3, 1998.

BACKGROUND

1. Field of the Invention

The present invention relates to probes useful in endoscopy and other procedures, and more particularly to balloon probes adapted to obtain spectroscopic information in the infrared spectral region. The invention also relates to methods that utilize these probes to analyze a surface of interest in connection with the diagnosis and treatment of disease.

2. Description of the Background

Numerous minimally-invasive diagnostic and treatment devices and methods of using them have been developed. Two such categories of devices are endoscopes and balloon catheters.

Endoscopes have proved useful in the examination of internal surfaces, in connection with various surgical and diagnostic procedures. However, conventional endoscopes, such as colonoscopes, gastroscopes, bronchoscopes, and angioscopes, are limited in their ability to detect all pathology present or provide unequivocal identification of abnormalities. These devices typically collect reflected visible light from a lumen, which may be expanded with water or gas, for simple visual evaluation of the tissue surface of interest. If a definitive diagnosis of the type of pathology or disease present in the tissue is needed, a tissue specimen is typically removed or biopsied and submitted for pathologic testing. Unfortunately, the biopsy process increases the risk of complications to the patient, such as hemorrhage, infection, and possible perforation of the organ or vessel under examination.

In addition to endoscopic devices that collect reflected visible light to produce an image allowing for simple visual evaluation, endoscopes that detect fluorescence emitted following excitation of tissue with a radiation source have also been described. One such device includes a visible light source, an optional endoscopic probe, optical sensors, a filter, a detector, and a display monitor. One or two wavelengths of visible light, preferably blue and red/near-infrared light, is directed to the tissue of interest, and remittance and autofluorescence is then detected, integrated/processed and displayed (U.S. Pat. No. 5,590,660 to MacAulay). This device does not incorporate balloons into the probes to facilitate optical coupling, to allow infrared-based evaluation of the diseased tissue.

Another device, useful for diagnosing the condition of GI tissue, utilizes fiber optics to detect emitted fluorescence following excitation radiation treatment (U.S. Pat. No. 5,421,337 to Richards-Kortum). In addition, devices which detect precancerous lesions using a mercury arc lamp endoscope (U.S. Pat. No. 5,647,368 to Zeng), devices which monitor and determine pre-existing physical properties of an organ by excitation with UV light (U.S. Pat. No. 5,456,252 to Vari), and devices which determine bilirubin concentration in tissue using reflectance spectroscopy (U.S. Pat. No. 5,353,790 to Jacques) have also been described. However, these devices do not combine balloon endoscopes with infrared radiation to detect diseased tissue.

Balloon catheters, like endoscopes, have been routinely used for diagnostics and treatment. Typical uses of conventional balloon catheters include procedures such as angioplasty and embolectomy. However, prior to the present invention, these conventional balloon devices could not be used in procedures in which infrared light is emitted in close proximity or directly onto a tissue surface, followed by collection of the light reflected or emitted from the tissue of interest, due to moisture and fluids in the surrounding environment.

The use of infrared radiation in catheters and endoscopic devices is complicated by the fact that water and most bodily fluids are opaque to infrared light. Consequently, even the slightest amount of moisture on the collection end of an endoscopic probe impairs the collection of infrared light. As a result, conventional endoscopes and balloon catheters cannot be used in infrared procedures where moisture or bodily fluids are present.

Fiber optic laser catheters and endoscopes having a protective shield over the probe tip have been described as useful in connection with the diagnosis and removal of atherosclerosis. In one such device, an optical fiber(s) carrying laser radiation is mounted in a catheter having a transparent protective optical shield over its distal end (U.S. Pat. Nos. 5,318,024 and 5,125,404 to Kittrell). The fiber(s) is anchored within the catheter so that there is an appropriate distance or space between the output end of the fiber(s) and the tip of the shield. The intervening space may be filled with fluid, optical surfaces may be optically contacted, or they may be anti-reflection coated to reduce reflections and maximize transmitted light. The catheter may be inserted into a blood vessel and the shield brought into contact with a plaque or obstruction site.

In this device, the protective optical shield mechanically displaces blood at the region to be analyzed and also protects the distal tip of the optical fiber(s) from intra-arterial contents. By locally displacing blood, the shield allows viewing of the tissue of interest without the need for a purge or flush. The optical shield may be in the form of glass, fused silica, sapphire or other optically transparent material. A flexible balloon over the tip of the probe may also be used as an optical shield. A different balloon may be used to provide an anchor point for positioning the catheter during use.

Although the shields of these devices protect a probe tip from blood contaminants, the use of a single balloon to both anchor and protect the tip of the probe from infrared opaque contaminants, which simultaneously allows optical coupling in the infrared region between the probe tip and the tissue surface has not previously been described. The Kittrel devices are designed for use with visible light. In addition, probes incorporating two anchoring balloons which allow the evacuation of a lumen and its subsequent filling with an infrared lucent coupling fluid are also not described.

As can be seen, because of the challenges posed by the effect of moisture on infrared light transmission, available endoscopic devices and catheters are limited in their ability to access and evaluate tissue and/or the lumen of vessels and organs using infrared light. There is therefore a need for a relatively non-invasive device which allows for optical coupling of a probe to the tissue or surface of interest, thereby allowing thorough evaluation and diagnosis of tissues and/or the lumen of vessels and organs using infrared radiation.

SUMMARY OF THE INVENTION

The invention overcomes the problems and disadvantages associated with current strategies and designs and provides new devices and methods for obtaining diagnostic information through the use of endoscopic balloon probes, particularly those utilizing infrared (IR) spectroscopy.

Probes according to a preferred embodiment of the present invention include an IR-transmitting single or multiple fiber endoscope, which is connected to a high resolution spectrometer. Infrared spectra are collected and used for diagnosis. The use of spectroscopy with a fiberoptic endoscope allows the collection of high resolution information in the infrared spectral region from diseased tissue. The present invention allows for rapid and accurate analysis of an organ, despite the presence of moisture, without the need for a tissue biopsy and its potential complications, such as hemorrhage, perforation and infection. In addition, by using the anchoring balloons in conjunction with the endoscopic probes, collection of diagnostic spectra, particularly infrared radiation, in the lumen of a vessel or organ is even further enhanced. The novel balloon configurations displace any opaque fluids which may be present and allow optical coupling of the probe to the tissue of interest.

In addition, multiple fibers may be paired with hyperspectral imaging techniques. Each fiber's data may be processed to provide a single pixel. The pixels produced by each individual fiber may be incorporated into an imaging array and/or translated into an image or other display optimized so that it may be readily interpreted or read by the user.

Accordingly, one embodiment of the invention is directed to a probe device which is useful for collecting infrared radiation from a surface of interest. The collected radiation is analyzed to provide information about the tissue surface. The probe device of this embodiment comprises a collection fiber which has a proximal end, a distal collection end opposite the proximal end adapted to collect infrared radiation, and an infrared conductive core located between the proximal end and the distal collection end. A sheath surrounds a portion of the collection fiber. A first anchoring balloon is preferably disposed on the sheath. The distal collection end of the collection fiber may be nested inside or disposed inside the balloon. This configuration displaces the opaque fluids which may be present, optically couples the probe to the tissue when the balloon is inflated, and protects the collection end of the probe from contamination.

Alternately, the first anchoring balloon may be disposed on the sheath between the proximal end and the distal collection end of the fiber and a second anchoring balloon may be disposed on a portion of the sheath that extends distally past the distal collection end of the collection fiber. When the two balloons are inflated, the void created between the balloons and the lumen wall may be filled with an infrared lucent fluid, displacing any infrared opaque fluids. This allows optical coupling of the collection end of the probe to the tissue surface, and protects the end of the probe from contamination.

Another embodiment is directed to a probe device having a plurality of collection fibers adapted to collect light, which is preferably infrared light. The probe device of this embodiment comprises an imaging collection fiber bundle comprising a plurality of collection fibers, each of the plurality of collection fibers comprising a proximal end, a distal collection end opposite the proximal end, and a conductive core located between the proximal end and the distal collection end. A first anchoring balloon is disposed on the fiber bundle; preferably it is disposed so that the distal collection ends of the plurality of collection fibers are disposed inside the balloon. Alternately, it may have the two balloon configuration previously described.

Another embodiment is directed to an endoscopic probe having a collection fiber which has a proximal end, a distal collection end opposite the proximal end adapted to collect infrared light, and a conductive core located between the proximal end and the collection end. The probe also has an illumination fiber having a distal illumination end adjacent the distal collection end of the collection fiber, and a proximate end coupled to the illumination source. An infrared lucent anchoring balloon is positioned on the probe such that the distal collection end of the collection fiber and the illumination end of the illumination fiber is disposed in the balloon. The illumination fiber preferably provides infrared light.

Another embodiment of the invention is directed to an endoscopic probe comprising a toroidally-shaped anchoring balloon, having a central hole or bore therethrough, and a collection fiber adapted to collect infrared radiation. The fiber has a distal collection end disposed inside the central hole of the balloon.

The present invention is also directed to methods for obtaining information about a surface of interest. One such method comprises the steps of positioning a probe adjacent to the surface of interest, collecting infrared light using the probe, transmitting the infrared light from the surface to analyzing means, and analyzing the infrared light to determine one or more properties of the surface. In this embodiment, the probe preferably comprises a collection fiber, the collection fiber comprising a proximal end, a distal collection end opposite the proximal end adapted to collect infrared light, and an infrared conductive core located between the proximal end and the distal collection end, and at least one anchoring balloon disposed on the probe.

Another embodiment is directed to a method for obtaining information about a surface of interest, comprising the steps of positioning a probe adjacent to the surface of interest, collecting infrared light using the probe, transmitting the infrared light from the surface to analyzing means, and analyzing the light to determine one or more properties of the surface. In this embodiment, the probe preferably comprises a light collection fiber bundle comprising a plurality of collection fibers adapted to collect infrared light, each of the plurality of collection fibers having a proximal end, a distal collection end opposite the proximal end, and a conductive core located between the proximal end and the distal collection end. A first balloon may be positioned on a sheath between the proximal end and the collection end of the plurality of collection fibers and a second balloon disposed on the sheath distal to the collection ends. Alternately, a balloon may be disposed on the probe such that the distal collection ends of the fibers lie inside the balloon.

Still another embodiment is directed to a method for obtaining information about a tissue surface, comprising the steps of collecting infrared radiation from the tissue surface using a probe placed proximate to the tissue surface, the probe having a longitudinal axis, transmitting the infrared radiation from the tissue surface to a remote analyzer, and analyzing the infrared information to determine properties of the tissue. The remote analyzer may comprise a spectrometer and detector array.

Although preferred embodiments of the invention are directed to probes having fibers and optical coupling means uniquely suited for the collection and analysis of infrared wavelengths, as will be clear to those of skill in the art, in other embodiments, additional fibers may be incorporated into the probes, so that other wavelengths (in addition to infrared) may be collected and analyzed.

Other objects and advantages of the invention are set forth in part in the description which follows, and in part, will be obvious from this description, or may be learned from the practice of the invention.

DESCRIPTION OF THE INVENTION

As embodied and broadly described herein, the present invention is directed to probe devices useful in a wide variety of medical and other procedures, including, but not limited to, endoscopic procedures such as thoracoscopy, laparoscopy, angioscopy and biopsy. Specifically, the present invention relates to balloon probes adapted to obtain spectroscopic information in a desirable spectral range, such as in the infrared spectral region. The invention also relates to methods that utilize these probes to analyze a surface of interest, such as in connection with the diagnosis and treatment of disease.

The present invention overcomes the problems inherent in the use of infrared radiation in a moist environment by providing novel means for bringing the collection end of the optic fiber into unobstructed optical contact with the tissue surface. The novel balloon configurations prevent interference with infrared excitation and collection due to moisture, which has made the use of infrared radiation in conventional scopes impossible.

Probes according to the present invention are advantageous in that they may be used to detect the composition or other qualities of a tissue surface in a non-invasive manner. For example, by detecting the frequencies and intensities of infrared light reflected or emitted from the wall, information about chemical bond energies can be obtained in a non-invasive manner. This bond energy information can then be translated into information about the composition of the wall and used as a diagnostic aid.

The probe devices and methods of the present invention can be used to determine tissue viability (i.e., whether tissue is dead or living, and whether it is predicted to remain living), detecting tissue ischemia (e.g., in heart, or in leg after a gunshot wound), differentiating between normal and malignant cells and tissues (e.g., delineating tumors, dysplasias and precancerous tissue, detecting metastasis), differentiating between infected and normal (but inflamed) tissue (e.g., extent of aortic root infection), quantification and identification of pathogens, and differentiating and delineating other pathologic states. Applications further include evaluation of tissue and blood chemistry, as well as examining the chemistry of blood vessel walls, including lipid and plaque characteristics and determining effects of lipid-lowering agents.

The probes and apparatus of the present invention may also be applied by veterinarians to animals, by dentists to dental applications, such as periodontal disease, and by pathologists in connection with forensic evaluation of a tissue of interest.

In addition, instruments according to the invention permit a surgeon or a physician to diagnose a medical condition or develop a surgical strategy based on real-time spectroscopic information obtained during surgery or in the course of performing clinical procedures or other medical evaluations. As a result, the physician is able to readily obtain significantly more information about a patient's condition than he or she might otherwise have been able to obtain. This additional information may permit a given surgical procedure to be carried out more efficiently, leading lead to more successful surgical results.

The general-purpose nature of instruments according to the present invention can help a surgeon develop significant amounts of medical information in time-critical surgical situations. For example, a patient may undergo surgery during which the surgeon may wish to evaluate a tumor, an area of blood vessel abnormality, or another pathological condition. Using the present invention, the physician can quickly determine the nature and extent of the pathology while the patient is still under anesthesia. This is particularly beneficial during major surgery, where significantly extending surgery duration increases morbidity and mortality risk. Because the devices of the present invention allow for rapid and minimally invasive procedures, the patient's overall risk is reduced. The immediate diagnosis and evaluation possible using the devices of the present invention provide significant benefits to the patient.

Figure 1:
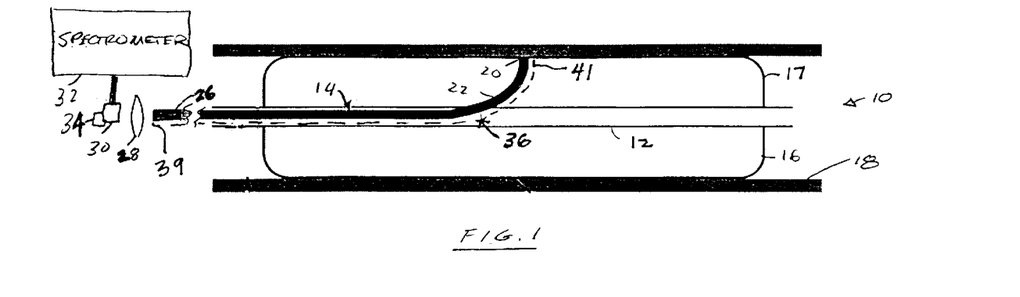
FIG. 1 Longitudinal cross-section of a probe device according to a first embodiment of the present invention, showing an illumination fiber in phantom.

A preferred embodiment of one probe device according to the present invention is depicted in FIG. 1. In the figures, like reference numerals refer to like features or elements so that a further description thereof is omitted. Referring to FIG. 1, probe or probe device 10 includes a sheath 12, an optical fiber 14, and a balloon 16. Balloon 16 has a wall 17. Sheath 12 is a flexible hollow tube that allows optical fiber 14 of probe 10 to be threaded along a guide wire inserted by a physician, although rigid or semi-rigid probes that do not require a guiding mechanism may also be used. A needle or other suitable means may also be used to guide the probe into place.

Suitable optical fibers useful in the present invention include, but are not limited to infrared fibers, such as fluoride-based glasses, chalcogenide glass fibers, sulfide-based fibers and telluride-based fibers. In a preferred embodiment, fluoride-based glass fibers are used. In another embodiment, chalcogenide glass fibers with low optical loss in the 2–11 $\mu$m wavelength region are used. Another embodiment of the invention may incorporate sulfide-based fibers, which transmit in the 1–6 $\mu$m region. Alternately, another embodiment may use telluride-based fibers which transmit in the 2–11 $\mu$m region. In yet another embodiment, mixtures of fibers may be used. Current minimal optical loss for glass cladded sulfide fibers is 0.4 dB/m at 2.6 $\mu$m. The minimal optical loss for telluride fibers is 0.7 dB/m at 6.6 $\mu$m. An anti-reflection (AR) coating may be applied to fiber end faces to increase transmission.

Optical fiber 14 includes a distal optical collection end 20 and a proximal optical end 26, and may include a bend 22. Distal collection end 20 is responsive to a surface of tissue of a patient. Bend 22 is preferably disposed proximate to collection end 20, between collection end 20 and proximal optical end 26. Proximal optical end 20 is optically coupled to spectrometer 32, such as by lens 28. Spectrometer 32 is coupled to optical detector 30. Spectrometer 32 is used to select one or more desired wavelengths which are transmitted to an optical detector 30 for measurement.

In the embodiment of FIG. 1, balloon 16 may be a standard angioplasty balloon designed for application to blood vessels. However, balloons of other sizes and shapes may also be employed depending on the intended application. Preferably, the balloon is infrared lucent or virtually infrared lucent when inflated. For example, teflon may be used to make a suitable balloon. By making the balloon very thin when inflated, any minor opacity to infrared light may be digitally subtracted from the signal using known techniques.

As shown in FIG. 1, when inserted, collection end 20 of the optical fiber 14 is disposed inside the lumen of balloon 16. Collection end 20 may directly contact the balloon wall. Alternately, there may be a gap between collection end 20 and the balloon wall 17 when the balloon is inflated.

In operation, probe 10 is inserted into an opening, such as an orifice or incision in a patient, and it is threaded until collection end 20 of the fiber is positioned (inside balloon 16) proximate or adjacent to the exposed tissue surface of interest. Balloon 16 is then inflated, such as via an inflation channel in sheath 12 with an infrared lucent gas or liquid. A preferred infrared lucent fluid is dry nitrogen gas. However, the media or medium chosen may be determined by the specific purpose and location of the procedure. Following inflation, collection end 20 is brought into close proximity or is optically coupled to the exposed tissue wall or surface of interest 18.

The optical coupling provided by the balloons of the invention allows the collection end of the probe to emit and collect infrared light unimpeded by infrared opaque fluids, such as water, blood or other bodily fluids. For example, the surface may be a lumen wall such as the wall of a blood vessel, the lining of an intestine, a chamber of the heart (e.g., to look for signs of rejection), or other appropriate lumen wall in the patient. The surface to be examined can also be created by an incision, such as an incision in the breast. The probes of the present invention may be used in procedures examining body cavities or any type of lumen, including fetoscopic and laparoscopic procedures.

Bend 22 in the fiber permits collection end 20 to collect light from a radial direction with respect to the longitudinal axis of the core of fiber 14. In radial-looking embodiments, a mirror or prism may optionally be used to collect light at an angle to the longitudinal axis of the fiber core. Alternatively, a fiber with a straight end may be used to collect light from a direction aligned with the longitudinal axis of the fiber.

By inflating the balloon with an infrared lucent fluid, collection end 20 of fiber 14 is optically coupled to the tissue surface 18. Light, including, but not limited to, infrared radiation emitted from or reflected by the wall, is thus transmitted along fiber 14 to the spectrometer and detector by total internal reflection (TIR). In a preferred embodiment, detector 30 is sensitive in the infrared spectral regions, allowing spectrometer 32 to present an infrared image or spectrum to the surgeon. Detector 30 is preferably sensitive to wavelengths of at least 800–25,000 nanometers (nm) and more preferably, to wavelengths ranging from 3,000–14,000 nm, and most preferably, to wavelengths of 6,000–12,000 nm. The acquired spectrum may be presented directly to a physician or it may be analyzed by a computer to assist in identifying attributes of the tissue surface.

The light received by collection end 20 of fiber 14 may be supplied to the area of interest from source 34 through illumination fiber 36. Illumination fiber 36 has a proximate end 39 optically coupled to light source 34, and a distal illumination end 41 adjacent to collection end 20. The light may also be emitted from within the tissue surface itself (e.g., bioluminescence), or it may be transmitted through the tissue surface from the other side of the tissue surface. By using fibers which are transparent in the ultraviolet region, further spectral information, including information attributable to fluorescence, may be obtained. Optionally, as will be clear to those of skill in the art, a single fiber may be used to both illuminate and collect, for example, by using a beam splitter to allow both excitation and collection with a single fiber.

Spectrometers useful in the present invention include dispersive, fixed or tunable bandpass devices. Preferred spectrometers include Fourier transform interferometers or dispersive monochromators. Useful imaging spectrometers include dielectric bandpass filters and liquid crystal tunable filters (LCTFs). The spectrometer and detector may be incorporated into a single device. Preferred illumination sources include infrared ceramic sources, such as a globar, or tunable infrared lasers. Other illumination sources include quartz tungsten halogen (QTH) bulbs (near infrared) and broad band visible bulbs.

Figure 2:
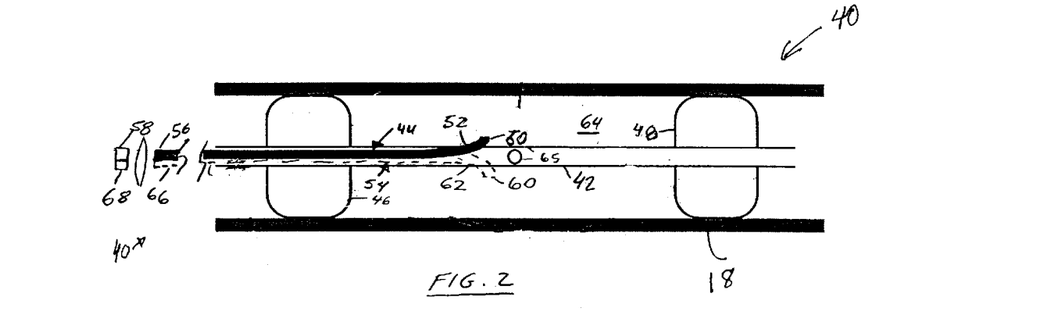
FIG. 2 Longitudinal cross-section of a probe device according to a second embodiment of the present invention, showing a multi-fiber configuration in phantom.

FIG. 2 depicts a second embodiment of the present invention. Referring to FIG. 2, second probe device or probe 40 includes sheath 42, optical fiber 44, proximate balloon 46 and distal balloon 48. Optical fiber 44 includes distal optical collection end 50, proximal optical end 56, and bend 52 disposed proximate to collection end 50. Probe 40 may differ from probe 10 in that the collection end 50 is not in apposition with or disposed inside the balloon, but instead sits between the distal and proximate balloons. The collection ends of probe 40 may or may not be in apposition with tissue surface 18. Sheath or conduit 42 also includes opening 65 which connects or allows communication between the inside of sheath 42 with volume 64. Volume 64 is defined by proximate balloon 46, distal balloon 48, and tissue surface 18. Proximal optical end 56 of fiber 44 is functionally coupled to detector 58, such as a detector array, via a spectrometer.

Probe 40, like probe 10 of the first embodiment, may be implemented as a single-fiber or multi-fiber probe by providing one or more additional fibers 54 that run next to first fiber 44 in a bundle. Fibers 54 may each include a bend 62 in a different plane causing fibers 54 to diverge radially from first fiber 44 and from each other. Alternately, the fibers may have axially offset bends 62 in the same plane. Each of the fibers 54 has a distal collecting end 60 and a proximate end 66, which may be coupled to an additional detector 68 via a spectrometer. The first detector 58 and the additional detector(s) 68 may form part of a detector array, such as a focal plane array (FPA). Alternately, the multiple fibers in this embodiment may be serviced by a single detector and an optical multiplexer.

In operation, probe 40 is positioned in the area of interest, and distal and proximate balloons 46 and 48 are inflated. This creates cavity or enclosed volume 64 between the two balloons 46 and 48 and lumen wall 18. In a lumen where there is fluid flow, such as a blood vessel, the upstream balloon is preferably inflated first. With both balloons inflated and in place, an infrared transparent coupling fluid (i.e., a gas or liquid) may be introduced into the cavity 64 via opening 65 in sheath 42. This optically couples the collection end 50 or ends 50, 60 to surface 18 of the lumen wall. Radiation received at each fiber can then be transmitted to its respective detector 58, 68, and the signals received by the different detectors can be displayed, such as a linear circumferential image of the lumen wall 18, or otherwise processed.

Figure 3:
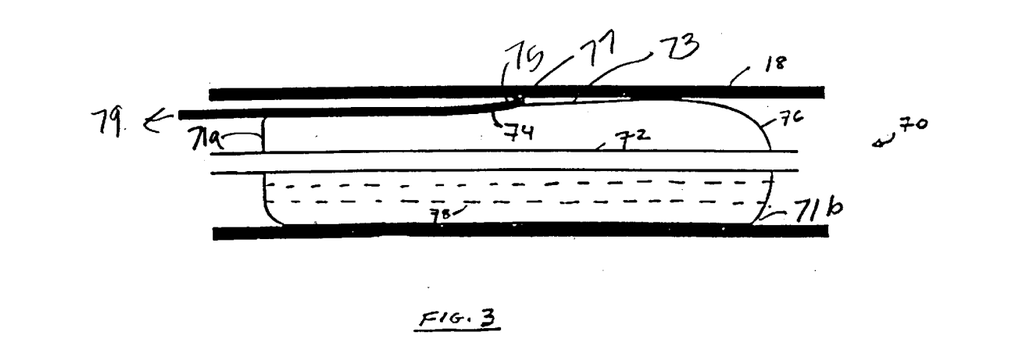
FIG. 3 Longitudinal cross-section of a probe device according to a third embodiment of the present invention.

FIG. 3 depicts a third embodiment of the present invention. Referring to FIG. 3, probe or probe device 70 includes sheath 72, balloon 76 and fiber 74. Fiber 74 has a distal collection end 77 and a proximal end 79. In this embodiment, the fiber or fibers may be, but need not be, fixed to an outer surface 73 of balloon 76. Probe 70 may further include a bend 75, or a reflector that redirects light from collection end 77 into the fiber 74. The fiber or fibers may be introduced separately from the balloon using a guidewire. Apposition to the wall may be accomplished by simple inflation of balloon 76.

Although probes 10, 40 and 70 are occlusive, probes 10 and 70 may employ an autoperfusion balloon to allow antegrade blood flow during inflation. The balloon may be toroidally shaped. The balloon may have a passage 78 that is either centrally located or offset from the center. For example, as depicted in FIG. 3, passage 78 allows fluid communication between proximate end 71a and distal end 71b of balloon 70. Probe 40 is less conducive to the addition of a passage, although a rigid sheath section may be provided that begins at the distal end of the distal balloon and ends at the proximate end of the proximal balloon.

Figure 4:
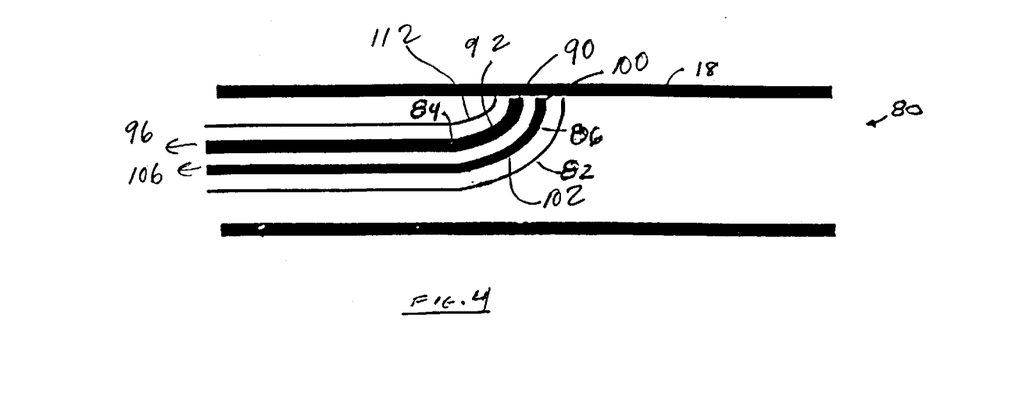
FIG. 4 Longitudinal cross-section of a probe device according to a fourth embodiment of the present invention.

FIG. 4 depicts a fourth embodiment of the present invention. Referring to FIG. 4, probe or probe device 80, which may be used as an angioscope, includes collection fiber 84, illumination fiber 86, and sheath 82. The two fibers 84 and 86 are arranged generally in parallel. Collection fiber 84 has a collection end 90, a bend 92, and a proximal end 96. Illumination fiber 86 has a distal end 100, a bend 102 and a proximate end 106. The two fibers are also surrounded by a flexible sheath 82 that is preferably smaller than the diameter of the lumen of interest, and includes a bend 112 that generally follows bends 82 and 92 in the two fibers. Like the other embodiments, probe 80 may include more than one collection fiber. In a preferred embodiment, probe 80 does not occupy the entire diameter of the lumen of interest, and therefore allows fluids such as blood to pass through the lumen while the assessment is being made. Alternately, this embodiment may be designed with an occlusion balloon or balloons and a perfusion lumen.

The embodiments described above preferably employ bends to orient the collection ends of the fibers, causing the light to be redirected by total internal reflection. However, any other suitable means for orienting the collection ends may be substituted for these bends. For example, in addition to bends, the means for orienting the collection of light may include mirrors, prisms or crystals to orient light collection by the fibers. Different coupling methods may also be employed to couple the light to the tissue surface and to couple light from the tissue surface into the fiber, such as lenses, prisms, or waveguides. For example, in one embodiment, an assembly made up of a looped fiber with a crystal tip at a bend in the loop is used to acquire light energy.

In various embodiments of the invention described herein which incorporate bends in the fibers, the probe may be inserted without the fiber or with the fiber retracted so that the area of the fiber with the bend lies within the sheath or analogous structure. After the probe is in position, the fiber may then be advanced out of the sheath (i.e., through a hole in the wall or an opening in the end of the sheath), causing the bend to deploy radially. For example, in one embodiment, a probe may comprise a collection fiber having an intrinsic bend. The fiber is moveably disposed in a sheath, such that the bend deploys as the distal end of the fiber is advanced through a hole in the sheath.

As will be clear to those of skill in the art, in the embodiment of FIG. 1, the balloon and fluid in the balloon function as part of the total optic system. The balloon is made so that it is preferably infrared lucent when inflated with infrared lucent fluid. As such, the illumination and collection of infrared light is virtually unimpeded. The balloons in the embodiments of both FIGS. 1 and 2 also function in preventing fouling of the optic fiber(s).

Balloons of the present invention may have a coating on their exterior surface that contacts the tissue of interest and interacts with said tissue. The balloon coating may comprise agents such as, for example, proteins, antigens, tissue stimulants, effector molecules and chemicals. The effect of contacting the tissue of interest with the balloon coating can then be analyzed according to the methods of the invention. The use of a coated balloon allows for a defined area to be impacted. Balloons of the present invention may also be useful in actively exciting or affecting a tissue of interest through effects such as changing the temperature of the tissue, or by distending, stretching or otherwise mechanically interacting with the tissue. By stretching or distending tissue, examination of tissue can be further optimized.

Preferably, the probes of the present invention are adapted to collect and analyze infrared light and preferably process images from image planes acquired at wavelengths in the infrared region. Optionally, the probe devices, including their detectors, may be sensitive to and capable of detecting and analyzing other spectra of light. For example, probes may alternately or additionally be sensitive to the visible and/or near infrared regions. The devices may operate in multispectral, and hyperspectral, or even ultraspectral imaging modes.

Multispectral modes involve image processing derived from a relatively small number of spectral image planes (two wavelengths to about twenty wavelengths). Hyperspectral and ultra spectral imaging modes involve at least twenty image planes and can produce significantly more accurate and informative results. Ultraspectral modes involve hundreds of wavelengths, and may be able to produce even further information about the surface under analysis. Hyperspectral imaging may include selecting specific wavelength bands for discrimination of a particular diseased state, or it may also allow the instrument to scan for multiple conditions at the same time.

The probe devices of the present invention, which are designed to collect and analyze specific wavelengths, have a number of potential applications. For example, wavelengths of about 550 and wavelengths of about 575 associated with oxy- and deoxy-hemoglobin may be collected and evaluated to determine blood oxygenation. The relationship between these wavelengths is described in "Hemoglobin: Molecular Genetics and Clinical Aspects," by H. Franklin Bunn and Bernard Forget, W. B. Sanders, 1986. Another example would involve the collection and analysis of the Fourier transform infra-red spectra of the colon and rectum as described in "Human Colorectal Cancers Display Abnormal Fourier Transform Spectra," by Basil Rigas et al., Proceedings of the National Academy of Science, pp. 8140–8144, 1987. As will be clear to those of skill in the art, the probe devices of the present invention may be designed to collect and analyze other wavelengths, depending on the intended application.

One embodiment of the present invention is directed to a probe device adapted to collect and analyze infrared radiation. The probe device comprises a collection fiber, the collection fiber comprising a proximal end, a distal collection end opposite the proximal end adapted to collect infrared radiation, and an infrared conductive core located between the proximal end and the collection end. Preferably, the fiber is flexible. A sheath surrounds a portion of the collection fiber, and a first anchoring balloon is disposed on the sheath. The probe device may further comprise a spectrometer optically coupled to the proximal end of the collection fiber and a detector, such as a detector array, functionally coupled to the spectrometer, to detect infrared radiation from the proximal end of the collection fiber. For example, a detector such as a mercury cadmium telluride (MCT) detector may be optically coupled to the spectrometer. Alternately, if the light is predispersed (i.e., the spectrometer is on the source rather than the detector), a detector element functionally coupled to the proximal end of the collection fiber may be disposed at or near the collection end of the collection fiber, and may even contact the surface of interest.

The instrument may further include a processing circuit functionally connected to the radiation detector. The processing circuit is preferably operative to translate the level of detected radiation into a measurable signal that is indicative of the level of damage or disease in the tissue. The signal may be directly evaluated, or it may be compared to stored reference profiles, to provide an indication of changes from previous levels or trends in the patient's health or disease state.

The probe preferably has an illumination fiber which has a distal illumination end adjacent or in close proximity to the distal collection end of the collection fiber and a proximate end optically coupled to an illumination source. Preferably, the illumination fiber is an infrared transmitting fiber, and the illumination source is an infrared source such as a globar. The sheath preferably surrounds a portion of both the collection fiber and the illumination fiber. Alternately, the collection fiber may comprise a beam splitter, which allows both excitation and collection of infrared light by a single collection fiber.

Rather than the use of an illumination fiber and remote illumination source, the probes of the present invention may alternately comprise a light source attached at the end of the probe or otherwise contained within the balloon. The balloon may also serve as an optical filter for both the illumination light as well as the collected light. Alternately, a light source may be provided from a separate source located on one side of the tissue of interest, while the probe is located on the other side of the tissue. In this embodiment, the probe and the light source effectively create a sandwich, with the tissue of interest in the middle, thereby allowing transmitted light to be collected by the probe. This sandwich embodiment also allows for volumetric analyses to be carried out on the tissue, in addition to surface assessment.

An optical coupler, such as a curved or focusing mirror or a lens may be used to optically couple the proximal end of the collection fiber to the spectrometer. The spectrometer is used to select one or more wavelengths which are transmitted to a detector, such as a detector array.

The collection end of the fiber is preferably adapted to collect light radiating or reflecting in a radial direction with respect to the longitudinal axis of the fiber. To accomplish this, the probe device preferably includes means proximate the collection end to orient the collection end in a radial direction with respect to a longitudinal axis of the fiber core. This may be accomplished, for example, by a bend in the fiber core. Other means for orienting the collection of infrared light by the fiber, in addition to bends, include mirrors, prisms and crystals.

An advantage of the present invention is the ability to obtain information in a lumen or other area where space is restricted. In one embodiment, the total diameter of the collection fiber, sheath and balloon are small enough to permit them to be inserted into mammalian blood vessels. For example, the total diameter of the collection fiber, sheath and balloon may have a diameter of less than 4 mm, and more preferably, less than 2 mm when the first balloon is maximally inflated. Alternately, the balloons may be designed so that they can be used in the lumen of a larger organ, such as intestine. For example, the balloon or balloons may have a diameter greater than 1–5 cm.

The collection fiber may be disposed in a variety of ways with respect to the first balloon. For example, in one embodiment, the collection fiber penetrates the wall of the balloon between the collection end and the proximal end such that the distal collection end lies inside the balloon. Alternately, the collection end of the collection fiber may be positioned adjacent to the outside of the wall of the balloon. A plurality of collecting fibers may be disposed in the sheath and used to collect radiation. In embodiments involving multiple collecting fibers, the fibers may surround the balloon, or the collection ends may be disposed inside the balloon. In embodiments where the collection end or ends lie inside the balloon, the balloon and the liquid or gas used to inflate the balloon are preferably infrared lucent.

The probe device may alternately include a second anchoring balloon disposed on a portion of the sheath that extends distally past the collection end of the collection fiber (i.e., it extends in a direction opposite the proximal end of the probe device). In this embodiment, the first balloon is disposed on the sheath between the proximal end and the collection end of the collection fiber and the second balloon is disposed on the distal portion of the sheath. An opening may be disposed in the sheath between the first and the second balloons. When this probe device is disposed in a lumen, the balloons may be inflated, and a fluid, preferably an infrared transparent or lucent fluid, is infused through the opening in the sheath to fill the void defined by the first and second balloons and the wall of the lumen.

As noted, it may be desirable to allow fluid flow past the probe device. In such instances, for example, those with a single balloon, a passage may be provided through the balloon to allow fluid communication between the proximate end and the distal end of the balloon.

Another embodiment of the present invention is directed to a probe device having an imaging collection fiber bundle comprising a plurality of collection fibers, each of the plurality of collection fibers comprising a proximal end, a distal collection end opposite the proximal end, and a conductive core located between the proximal end and the collection end. A first anchoring balloon is disposed on the fiber bundle. The probe device may further comprise a spectrometer and a detector, such as a detector array, responsive to the proximal end of the plurality of collection fibers to acquire an image. The collection fibers preferably conduct infrared light, but other fibers may be used which conduct other wavelengths of light such as visible, UV and/or near infrared light. As with the previous embodiment, the probe device may include an illumination fiber having a distal illumination end adjacent the collection ends of the collecting fibers.

In one embodiment of a multi-fiber probe, there may be a central illumination fiber surrounded by multiple collection fibers. For example, six collection fibers (or any desired number) may be placed circumferentially around a center illumination fiber in a hexagonal configuration, and may be oriented to efficiently collect the light. In another embodiment, a multi-fiber probe may comprise a plurality of collection fibers and a plurality of illumination or excitation fibers; in this embodiment each of the collection fibers may be associated with or disposed adjacent to its respective excitation fiber.

With respect to multi-fiber embodiments, the light or data collected by each fiber may provide a single pixel of information for incorporation into an image or other display. The image is preferably optimized to facilitate interpretation. For example, a two dimensional planar image may be produced from circumferential data.

A novel feature of balloon probes according to various embodiments of the invention relates to the incorporation of the balloon into the actual optical path. For example, in one embodiment, the distal collection ends are disposed inside the wall of the balloon. This balloon is made of an infrared lucent material (or is virtually infrared lucent due to its thickness when inflated) and filled with an infrared lucent fluid to form a part of the optical path in a single fiber probe. In multiple fiber probes, this balloon may be compartmentalized. In the latter embodiment, the balloon may be partitioned into a plurality of different or separate sacs or compartments. The collection ends of the collection fibers are each disposed in a separate compartment.

In multi-fiber embodiments incorporating two anchoring balloons, the first balloon may be disposed between the proximal and distal collection ends of the collection fibers. Further, a conduit may be provided, which passes through a first anchoring balloon, and has a portion which extends distally past the distal collection end of the plurality of collection fibers. This embodiment has a second anchoring balloon attached to the portion of the conduit that extends distally past the distal collection end of the plurality of collection fibers. An opening may be provided in the conduit between the first and second balloons allowing fluid communication with the space between the first and second balloons.

With respect to single balloon embodiments, the plurality of collection fibers in the fiber bundle may be positioned adjacent to the outside of the wall of the balloon, and may form a bundle that surrounds the balloon. Alternately, the distal collection ends of the plurality of fibers may be disposed inside the wall of the balloon, and the balloon may serve as part of the coupler and collection device. In this embodiment, the collection ends are preferably close to or contact the balloon wall in operation. The balloon may be partitioned into a plurality of separate compartments with the collection ends each disposed in a separate compartment.

The fiber bundle may be flexible, and may include means proximate the collection end of each fiber to orient the collection ends in a radial direction with respect to the axis of the core of the fibers, such as bends in the fiber cores. Mirrors, prisms and crystals may also be used as a means for orienting collection of light. In a preferred embodiment, the bends in the fiber cores orient the plurality of collection fibers in at least two different directions.

In this embodiment, the detector may comprise a focal plane array such as a mercury cadmium telluride plane array or a microbolometer array. The device may further comprise an optical multiplexer such as a digital micro mirror array.

Instruments according to the present invention may also include imaging optic means within the probe, a spectral separator optically responsive to the imaging optic means, and an imaging sensor optically responsive to the spectral separator. The spectral separator may be a tunable filter and the imaging sensor may be a two-dimensional imaging array, such as a focal plane array. The instrument may optionally comprise a diagnostic processor having an image acquisition interface responsive to the imaging sensor. The diagnostic processor may also have a filter control interface to which the spectral separator is responsive.

The diagnostic processor may also include a general-purpose processing module and diagnostic protocol modules, which may each include filter transfer functions and an image processing protocol. The general-purpose processing module may be operative to instruct the filter to successively apply the filter transfer functions to light collected from the patient, to acquire from the imaging sensor a number of images of the collected light each obtained after one of the filter transfer functions is applied, and to process the acquired images according to the image processing protocol to obtain a processed display image. The general-purpose processor may be a real-time processor operative to generate a processed display image within a time period on the order of the persistence of human vision. It may also be operative to acquire some images more slowly depending on the number of wavelengths and complexity of diagnostic processing protocol. The sensor and filter may be operative in the visible, infra-red, and UV regions.

In embodiments involving multiple fibers, light from each fiber may be processed to generate an individual pixel for that fiber. The pixels may then be arranged so that they form an image or display which can be readily interpreted or read by the user.

Another embodiment of the invention is directed to an endoscopic balloon probe having an infrared light source. This embodiment includes a collection fiber, the collection fiber comprising a proximal end, a distal collection end opposite the proximal end adapted to collect infrared light, and a conductive core located between the proximal end and the distal collection end, an illumination fiber having a distal illumination end adjacent the distal collection end of the collection fiber, and a proximate end coupled to an infrared illumination source such as globar or other means to orient image collection. An anchoring balloon is disposed on the probe such that the distal collection end of the collection fiber and the distal illumination end of the illumination fiber are disposed inside the balloon. Preferably the balloon is infrared lucent. A sheath may surround a portion of the collection fiber and a portion of the illumination fiber. The collection fiber may have a bend to orient the collection end in a radial direction with respect to the axis of the conductive core, or may use other means to orient image collection.

The present invention is also directed to novel methods for analyzing or obtaining information about the properties of a tissue or other surface of interest. One such method for obtaining information about a surface of interest comprises the steps of positioning a probe adjacent to the surface of interest, collecting infrared light using the probe, transmitting the infrared light from the surface to analyzing means, and analyzing the light to determine one or more properties of the surface. The probe preferably comprises a collection fiber, the collection fiber comprising a proximal end, a distal collection end opposite the proximal end adapted to collect infrared light, and an infrared conductive core located between the proximal end and the distal collection end, and a first anchoring balloon disposed on the probe. The step of collecting infrared light preferably comprises collecting infrared light in the vicinity of the collection end of the probe that shines or radiates in a direction generally or substantially perpendicular to the longitudinal axis of the probe. The step of analyzing preferably comprises spectroscopic analysis. More preferably, the step of analyzing comprises imaging spectroscopy.

In a preferred method, the distal collection end of the probe lies inside the balloon, and the balloon protects the collection end of the probe from moisture and fouling. Alternately, the probe further comprises a sheath which surrounds a portion of the collection fiber. A first anchoring balloon is disposed on the sheath between the proximal and distal collection end of the collection fiber. The sheath has a portion that extends distally past the collection end of the collection fiber, and the probe further comprises a second anchoring balloon disposed on the portion of the sheath distal to the collection end. When the tissue of interest is disposed in a lumen, the method may further comprise the steps of inflating the first balloon and the second balloon to create an enclosed volume defined by the first balloon, the second balloon and the lumen, and completely or partially filling the volume with a fluid, such as dry nitrogen gas. The balloons may be inflated sequentially to facilitate this process. For example, when the probe is inserted in a blood vessel, the upstream balloon may be inflated first, followed by the downstream balloon. The upstream balloon may be the first or the second balloon, depending on whether the probe is inserted antegrade or retrograde into the vessel. The fluid used to fill the volume may be an infrared lucent gas or liquid, including optical coupling fluids such as dry nitrogen gas. In a preferred embodiment of the method, the distal collection end of the collection fiber is inserted into the enclosed volume after the balloons are inflated and the volume is filled with liquid.

Another embodiment is directed to a method for obtaining information about a surface of interest comprising the steps of positioning a probe adjacent to the surface of interest, collecting light using the probe, transmitting the light from the surface to analyzing means, and analyzing the light to determine one or more properties of the surface. Preferably, the probe comprises a light collection fiber bundle comprising a plurality of collection fibers adapted to collect infrared light, each of the plurality of collection fibers comprising a proximal end, a distal collection end opposite the proximal end, and a conductive core located between the proximal end and the distal collection end. The probe is preferably adapted to collect infrared light. The step of collecting light preferably comprises collecting light in the vicinity of the collection end of the probe that radiates or shines in a direction generally or substantially perpendicular to the longitudinal axis of the probe. The step of analyzing preferably comprises spectroscopic analysis, such as imaging spectroscopy, standard or otherwise. Preferably, an anchoring balloon is disposed on the probe such that the distal collection ends are disposed inside the wall of the balloon.

Alternately, the probe may further comprise a sheath disposed around the fiber bundle, a first anchoring balloon disposed on the sheath between the collection ends and the proximal ends of the plurality of fibers, and a second anchoring balloon disposed on the sheath distal to the collection ends of the plurality of fibers. As with the previous method, when the tissue of interest is disposed in a lumen, the method may further comprise the steps of inflating the first balloon and the second balloon to create an enclosed volume defined by the first balloon, the second balloon and the lumen, and emptying the volume or filling the volume with a fluid. The fluid is preferably infrared lucent. In a preferred embodiment of the method, the distal collection ends are inserted into the enclosed volume after the balloons are inflated and the volume is filled with the fluid.

Another embodiment of the invention is directed to a probe in which the distal collection end of one or more collection fibers is disposed in the central hole of a toroidally-shaped anchoring balloon. This embodiment may optionally comprise one or more illumination or excitation fibers disposed so that the distal illumination end of the fiber or fibers are also disposed in the central hole of the balloon. In these embodiments, excitation light from the distal illumination end of the illumination fiber passes through the inner wall of the balloon, the coupling fluid and the outer wall of the balloon to reach the tissue surface. Likewise, light coming from the tissue surface passes through the outer wall of the balloon, the coupling fluid and the inner wall of the balloon to reach the distal collection end of the probe.

Another embodiment of the present invention is directed to a method for obtaining information about a tissue surface, comprising the steps of collecting infrared radiation from the tissue surface using a probe placed proximate to the tissue surface, the probe having a longitudinal axis, transmitting the infrared radiation from the tissue surface to a remote analyzer, and analyzing the infrared information to determine properties of the tissue surface. The step of analyzing may comprise spectroscopic analysis, such as imaging spectroscopy, standard or otherwise. In addition, the step of collecting and transmitting may be performed using multiple fibers in the probe. The step of collecting infrared radiation may comprise collecting infrared light in the vicinity of a collection end of the probe that radiates or shines in a direction generally or substantially perpendicular to the longitudinal axis of the probe. Preferably, the probe has means for optically coupling the collection end of the probe to the tissue surface. Such means include all of the various balloon configurations previously described. For example, the means for optically coupling may comprise an anchoring balloon disposed around a collection end of said probe. Alternately, the means may comprise a first anchoring balloon and a second anchoring balloon disposed on said probe such that a collection end of said probe is positioned between said first and said second anchoring balloons. The two balloons may be inflated as previously described, thereby removing or minimizing the presence of infrared opaque substances between the tissue surface and probe tip.

In one embodiment, the method further comprises the step of providing a source of infrared radiation adjacent to the opposing surface of the tissue surface being analyzed, and the step of collecting comprises collecting the radiation transmitted through the tissue to the probe.

Although the preferred embodiments disclosed herein are directed to probes collecting infrared light, as will be clear to those of skill in the art, other forms of electromagnetic radiation, including but not limited to visible light, near-infrared light, or any desired wavelength may be collected by appropriate modifications to the probe. The balloons, sheaths, collection fibers and/or illumination fibers described herein may be disposable. In addition, although the probes of the invention have been described primarily as useful in connection with medical procedures, they may be used to evaluate any other desired surface.

Other embodiments and uses of the invention will be apparent to those skilled in the art from consideration of the specification and practice of the invention disclosed herein. All references cited herein, including all U.S. and foreign patents and patent applications, including, but not limited to, U.S. Provisional Patent Application Serial No. 60/098,957 and U.S. application Ser. No. 09/182,898, are specifically and entirely incorporated by reference. The specification and examples should be considered exemplary only with the true scope and spirit of the invention indicated by the following claims.

We claim:

1. A probe, comprising:
   one or more infrared transparent fibers, each fiber comprising:
      a proximal end;
      a collection end opposite the proximal end; and
      a conductive core which is conductive to radiation and located between the proximal end and the collection end;
   a balloon positioned relative to the one or more fibers and proximate the collection end of the one or more fibers;
   a source of infrared lucent fluid; and
   a detector responsive to radiation from the proximal end of the one or more fibers.

2. The probe of claim 1, wherein the balloon is toroidally shaped.

3. The probe of claim 1, wherein the balloon comprises a thin layer of material that is infrared lucent when inflated with a nitrogen gas.

4. The probe of claim 1, wherein the collection end of the one or more fibers is positioned inside the balloon such that said collection end presses against a wall of the balloon.

5. The probe of claim 1, wherein the conductive core further comprises a turn for changing a direction of radiation along said conductive core wherein the turn comprises a bend, mirror, crystal or prism.

6. The probe of claim 1, wherein the one or more fibers comprise a material that is transparent to radiation between 0.8 and 25 microns.

7. The probe of claim 1, further comprising a source of infrared radiation.

8. The probe of claim 1, further comprising an optical coupler for optically coupling said one or more infrared transparent fibers to a spectrometer.

9. The probe of claim 8, wherein the optical coupler comprises a lens.

10. The probe of claim 1, wherein the one or more infrared transparent fibers are flexible.

11. The probe of claim 1, further comprising means proximate to said collection end to orient said collection end in a radial direction with respect to a longitudinal axis of said conductive core.

12. The probe of claim 11, where the one or more infrared transparent fibers are moveably disposed in a sheath and said means proximate to said collection end comprises a bend in said conductive core, and wherein said bend deploys radially when said collection end is advanced through a hole in said sheath.

13. The probe of claim 1, further comprising means for orienting collection of infrared radiation by the one or more infrared transparent fibers, said means selected from the group consisting of a bend, a mirror, and a crystal.

14. The probe of claim 1, further comprising a detector element functionally coupled to said one or more infrared transparent fibers to detect infrared radiation from said proximal end of said one or more infrared transparent fibers, wherein said detector element is disposed at or near the collection end of the one or more infrared transparent fibers.

15. The probe of claim 1, wherein the balloon has a diameter of greater than 1 cm when said balloon is maximally inflated.

16. The probe of claim 1, wherein the balloon has a diameter of less than 4 mm when said balloon is maximally inflated.

17. The probe of claim 1, wherein the collection end of said one or more infrared transparent fibers is positioned in direct contact with a wall of said balloon.

18. The probe of claim 1, wherein the collection end of said one or more infrared transparent fibers is positioned adjacent to the outside of a wall of said balloon.

19. A probe comprising:
    one or more infrared transparent fibers in the form of a bundle, said bundle comprising:
       a proximal end;
       a distal collection end opposite said proximal end adapted to collect infrared radiation; and
       an infrared conductive core located between said proximal end and said distal collection end;
    a sheath for receiving at least a portion of said bundle, wherein said sheath has a distal portion extending beyond said distal collection end of said bundle;
    a first anchoring balloon disposed on said sheath between said proximal end and said distal collection end of said bundle;
    a second anchoring balloon disposed on said distal portion of said sheath; and
    a cavity between said first and second anchoring balloons, wherein said distal collection end is disposed in said cavity.

20. The probe of claim 19, further comprising an opening in said sheath between said first and said second anchoring balloons.

21. The probe of claim 19, wherein the first or second anchoring balloon further comprises a proximate end and a distal end, and a passage through said balloon to allow fluid communication between said proximate end and said distal end.

22. The probe of claim 19, further comprising a plurality of collecting fibers disposable at least partly in said sheath for collecting infrared radiation.

23. The probe of claim 19, further comprising an interactive coating on said first or second balloon.

24. The probe of claim 23, wherein the coating is selected from the group consisting of proteins, antigens, stimulants, effector molecules and chemicals.

25. The probe of claim 19, further comprising a display wherein radiation collected by each of said one or more infrared transparent fibers provides a single pixel for incorporation into said display.

26. The probe of claim 19, further comprising an image display wherein radiation collected by the plurality of one or more infrared transparent fibers is translated into an image on said image display.

27. The probe of claim 19, wherein the fiber bundle is flexible.

28. The probe of claim 19, further comprising means proximate to said distal collection end of at least one of said one or more fibers to orient said distal collection end in a radial direction with respect to a longitudinal axis of the conductive core.

29. The probe of claim 28, wherein the means proximate to said distal collection end to orient said distal collection end in a radial direction comprises a bend in said conductive core.

30. The probe of claim 29, wherein the bend in said conductive core orients said plurality of one or more infrared transparent fibers in at least two different directions.

31. The probe of claim 19, further comprising a detector which optionally comprises a focal plane detector array.

32. A probe comprising:
    one or more infrared transparent fibers, said one or more infrared transparent fibers comprising:
       a proximal end;

a distal collection end opposite said proximal end for collection of infrared radiation; and an infrared conductive core located between said proximal end and said distal collection end;

a sheath for receiving at least a portion of said one or more infrared transparent fibers;

an anchoring and protective balloon disposed on said sheath, wherein said balloon is infrared lucent and toroidally shaped, and protects said distal collection end from infrared contaminants;

an illumination fiber having a distal illumination end adjacent said distal collection end of said one or more infrared transparent fibers and a proximate end coupled to an illumination source; and a passage through said balloon to allow fluid communication between a proximal end and distal end of said balloon.

33. The probe of claim 32, wherein the sheath surrounds a portion of said one or more infrared transparent fibers and a portion of said illumination fiber.

34. A method for obtaining information about a surface of interest comprising the steps of:

positioning a probe adjacent to said surface of interest, said probe comprising:
a collection fiber, said collection fiber comprising a proximal end, a distal collection end opposite said proximal end for collection of infrared radiation; and
an infrared conductive core located between said proximal end and said distal collection end;
a first anchoring balloon disposed therein which is infrared lucent; and
a sheath surrounding a portion of said collection fiber wherein said first anchoring balloon is disposed on said sheath between said proximal end and said distal collection end, and said sheath extends distally past said distal collection end and wherein said probe further comprises a second anchoring balloon disposed on said sheath distal to said distal collection end, and wherein said surface of interest is disposed in a lumen;

inflating said first anchoring balloon and said second anchoring balloon to create an enclosed volume defined by said first anchoring balloon, said second anchoring balloon and said lumen;

filling said volume with a fluid;

collecting infrared radiation from said surface with said probe;

transmitting infrared radiation collected from said surface to analyzing means; and analyzing the infrared radiation with said analyzing means to determine one or more properties of said surface.

35. The method of claim 34, further comprising the step of distending the surface of interest by inflating said first anchoring balloon to optimize analysis of the surface.

36. The method of claim 34, wherein the first and second anchoring balloons are inflated sequentially.

37. The method of claim 34, wherein the fluid comprises an infrared lucent gas.

38. The method of claim 34, wherein the fluid comprises an infrared lucent liquid.

39. The method of claim 34, further comprising the step of inserting said distal collection end of said collection fiber into the enclosed volume after inflating said first and second anchoring balloons and filing the volume with said fluid.

40. A probe comprising:
one or more infrared transparent fibers, each fiber comprising:
a proximal end;
a collection end opposite the proximal end; and
a conductive core which is conductive to radiation and located between the proximal end and the collection end;
a balloon with a first opening along its length and a second opening midway along the length of the first opening, and extending from the midway point of the first opening to outside the balloon, and positioned at and covering the collection end wherein the one or more fibers at the collection end of the probe enter an end of the first opening of the balloon and exit the second opening to contact a sample surface adjacent to the balloon surface;
a source of a fluid to expand the balloon; and
a detector responsive to radiation from the proximal end of the one or more fibers.

41. The probe of claim 40, wherein the balloon comprises a thin layer of material that is infrared lucent when inflated with atmospheric gas.

42. The probe of claim 40, further comprising a turn for changing the direction of radiation wherein the turn comprises a bend, mirror, or crystal.

43. The probe of claim 40, wherein the one or more fibers comprises a material that is transparent to radiation between 3 and 14 microns.

44. A probe comprising:
one or more infrared transparent fibers, each fiber comprising:
a proximal end;
a collection end opposite the proximal end; and
a conductive core which is conductive to radiation and located between the proximal end and the collection end;
a balloon with an opening along its length to allow passage of body fluids wherein the one or more fibers at the collection end of the probe is attached to and located at the outer surface of a portion of the balloon without extending into the balloon;
a source of a fluid to expand the balloon; and
a detector responsive to radiation from the proximal end of the one or more fibers.

45. The probe of claim 44, wherein the balloon is toroidally shaped.

46. The probe of claim 44, wherein the conductive core further comprising a turn for changing the direction of radiation along said core wherein the turn comprises a bend, mirror, crystal or prism.

47. The probe of claim 44, wherein the one or more fibers comprises a material that is transparent to radiation between 6 and 12 microns.

48. The probe of claim 44, wherein the balloon comprises an infrared translucent material.

49. A method for obtaining spectral information from a body surface inside a lumen of the body using an infrared probe, the probe comprising:
one or more infrared transparent fibers, each fiber comprising:
a proximal end;
a collection end opposite the proximal end;
a conductive core which is conductive to radiation and located between the proximal end and the collection end; and a balloon with a first opening along its length and a second opening midway along the length of the first opening, and extending from the midway point of the first opening to outside the balloon, and positioned at and covering the collection end, wherein the one or more fibers at the collection end of the probe enter an end of the first opening of the balloon and exit the second opening to contact a sample surface adjacent to the balloon surface, and a fluid to expand the balloon, comprising:

positioning the probe inside the lumen and adjacent to the body surface; and    collecting radiation from the surface using the probe.

50. The method of claim 49, further comprising the step of distending the surface by inflating the balloon with the fluid.

51. A method for obtaining spectral information from a body surface inside a lumen of the body using a probe comprising:

one or more infrared transparent fibers, each fiber including:

a proximal end;

a collection end opposite the proximal end;

a conductive core which is conductive to radiation and located between the proximal end and the collection end;

a balloon with an opening along its length to allow passage of body fluids, wherein the one or more fibers at the collection end of the probe are attached to and located at the outer surface of a portion of the balloon without extending into the balloon; and    a source of a fluid to expand the balloon, comprising:

positioning the probe inside the lumen and adjacent to the body surface; and       collecting radiation from the surface using the probe.

52. The method of claim 51, further comprising the step of distending the surface by inflating the balloon with the fluid.

* * * * *